United States Patent  
Warlick

(10) Patent No.: US 12,402,898 B2
(45) Date of Patent: Sep. 2, 2025

(54) ACOUSTIC SHOCK WAVE OR PRESSURE PULSE TREATMENT FOR PROPTOSIS OR EXOPHTHALMOS

(71) Applicant: SoftWave Tisse Regeneration Technologies, LLC, Kennesaw, GA (US)

(72) Inventor: John F. Warlick, Kennesaw, GA (US)

(73) Assignee: Softwave Tissue Regeneration Technologies, LLC, Kennesaw, GA (US)

( * ) Notice: Subject to any disclaimer, the term of this patent is extended or adjusted under 35 U.S.C. 154(b) by 201 days.

(21) Appl. No.: 18/102,243

(22) Filed: Jan. 27, 2023

(65) Prior Publication Data

US 2024/0252190 A1 Aug. 1, 2024

(51) Int. Cl.
*A61B 17/22* (2006.01)
*A61C 19/06* (2006.01)

(52) U.S. Cl.
CPC ........ *A61B 17/22004* (2013.01); *A61C 19/06* (2013.01)

(58) Field of Classification Search
CPC .......................... A61B 17/22004; A61C 19/06
See application file for complete search history.

(56) References Cited

U.S. PATENT DOCUMENTS

| | | |
|---|---|---|
| 3,951,140 A | 4/1976 | Eggleton et al. |
| 4,539,989 A | 9/1985 | Forssmann et al. |
| 4,807,627 A | 2/1989 | Eisenmenger |
| 4,868,161 A | 9/1989 | Roberts |
| 4,905,671 A | 3/1990 | Senge et al. |
| 5,119,801 A | 6/1992 | Elzenhoefer et al. |
| 5,160,336 A | 11/1992 | Favre |
| 5,173,295 A | 12/1992 | Wehling |

(Continued)

FOREIGN PATENT DOCUMENTS

| | | |
|---|---|---|
| DE | 19721218 | 11/1998 |
| DE | 10311659 | 9/2004 |

(Continued)

OTHER PUBLICATIONS

Forstermann et al. 2006 Circulation 113:1708-1714 (Year: 2006).*

(Continued)

*Primary Examiner* — Keith M Raymond
*Assistant Examiner* — Patrick M Mehl
(74) *Attorney, Agent, or Firm* — David O. Simmons

(57) ABSTRACT

The device of the present invention allows for a method of treating a patient exhibiting proptosis of eye tissue by treating inflamed tissue behind the eye or treating the thyroid directly or treating a reflexology zone to reduce pressure and inflammation of the eye tissue using pressure pulses or shock waves. The treatment method for bulging eyes has the steps of placing an applicator head of an acoustic shock wave or pressure pulse generator or source on or near an eye or eyelid region, temple, thyroid or reflexology zone; coupling the applicator head directly or indirectly to an exposed surface of the region being treated; and activating the generator or source to emit pressure pulses or acoustic shock waves to the eye or eyelid region, temple, thyroid or reflexology zone to treat the eye tissue exhibiting high pressure and inflammation to reduce the pressure and inflammation.

11 Claims, 10 Drawing Sheets

(56) References Cited

U.S. PATENT DOCUMENTS

| | | | |
|---|---|---|---|
| 5,174,280 A | 12/1992 | Gruenwald et al. |
| 5,178,135 A | 1/1993 | Uchiyama et al. |
| 5,222,484 A | 6/1993 | Krauss et al. |
| 5,314,457 A | 5/1994 | Jeutter et al. |
| 5,316,000 A | 5/1994 | Chapelon et al. |
| 5,419,335 A | 5/1995 | Hartmann |
| 5,458,130 A | 10/1995 | Kaufman et al. |
| 5,545,124 A | 8/1996 | Krause et al. |
| 5,595,178 A | 1/1997 | Voss et al. |
| 5,670,372 A | 9/1997 | Hogan |
| 5,690,926 A | 11/1997 | Hogan |
| 6,036,661 A | 3/2000 | Schwarze et al. |
| 6,113,560 A | 9/2000 | Simnacher |
| 6,186,963 B1 | 2/2001 | Schwarze et al. |
| 6,190,336 B1 | 2/2001 | Duarte et al. |
| 6,217,531 B1 | 4/2001 | Reitmajer |
| 6,221,021 B1 | 4/2001 | Redano |
| 6,284,143 B1 | 9/2001 | Kerfoot |
| 6,368,292 B1 | 4/2002 | Ogden et al. |
| 6,390,995 B1 | 5/2002 | Ogden et al. |
| 6,413,230 B1 | 7/2002 | Haupt et al. |
| 6,544,987 B2 | 4/2003 | Guo et al. |
| 6,650,935 B1 | 11/2003 | Watmough |
| 6,723,534 B2 | 4/2004 | Lin |
| 6,879,713 B1 | 4/2005 | Keefe |
| 6,881,409 B2 | 4/2005 | Gold |
| 6,884,578 B2 | 4/2005 | Warrington et al. |
| 7,470,240 B2 | 12/2008 | Schultheiss et al. |
| 7,507,213 B2 | 3/2009 | Schultheiss et al. |
| 7,544,171 B2 | 6/2009 | Schaden et al. |
| 7,841,995 B2 | 11/2010 | Schultheiss et al. |
| 7,883,482 B2 | 2/2011 | Schultheiss et al. |
| 7,905,845 B2 | 3/2011 | Warlick et al. |
| 7,988,648 B2 | 8/2011 | Warlick et al. |
| 8,257,282 B2 | 9/2012 | Uebelacker et al. |
| 8,298,162 B2 | 10/2012 | Del Giglio |
| 8,535,249 B2 | 9/2013 | Uebelacker et al. |
| 9,506,035 B2 | 11/2016 | Williams et al. |
| 9,636,516 B2 | 5/2017 | Schwartz |
| 9,713,731 B2 | 7/2017 | Slayton et al. |
| 2002/0002345 A1 | 1/2002 | Marlinghaus |
| 2002/0077550 A1 | 6/2002 | Rabiner et al. |
| 2003/0129154 A1 | 7/2003 | McDaniel |
| 2003/0157024 A1 | 8/2003 | Tachibana et al. |
| 2004/0059265 A1 | 3/2004 | Candy et al. |
| 2004/0162508 A1 | 8/2004 | Uebelacker |
| 2005/0010140 A1 | 1/2005 | Forssmann |
| 2005/0038362 A1 | 2/2005 | Schultheiss |
| 2005/0075587 A1 | 4/2005 | Vago |
| 2005/0084519 A1 | 4/2005 | Miyazaki |
| 2006/0036195 A1 | 2/2006 | Schultheiss |
| 2006/0051328 A1 | 3/2006 | Johnson |
| 2006/0089673 A1 | 4/2006 | Schultheiss |
| 2006/0100550 A1 | 5/2006 | Schultheiss |
| 2006/0246044 A1 | 11/2006 | Lutz |
| 2006/0293708 A1 | 12/2006 | Voss |
| 2006/0293725 A1 | 12/2006 | Rubinsky et al. |
| 2007/0016112 A1 | 1/2007 | Schultheiss |
| 2007/0142753 A1 | 6/2007 | Warlick |
| 2007/0239072 A1 | 10/2007 | Schultheiss |
| 2007/0239082 A1 | 10/2007 | Schultheiss |
| 2008/0033323 A1 | 2/2008 | Meirer |
| 2008/0146971 A1 | 6/2008 | Uebelacker |
| 2011/0034832 A1 | 2/2011 | Cioanta |
| 2011/0087157 A1 | 4/2011 | Cioanta |
| 2012/0239055 A1 | 9/2012 | Spector |
| 2013/0197404 A1 | 8/2013 | Spector |
| 2017/0128496 A1 | 5/2017 | Willimas et al. |
| 2017/0209708 A1 | 7/2017 | Schwarz |
| 2017/0258676 A1 | 9/2017 | Lue |
| 2018/0221688 A1 | 8/2018 | Cioanta |

FOREIGN PATENT DOCUMENTS

| | | |
|---|---|---|
| EP | 0243947 | 4/1987 |
| EP | 0324711 | 1/1989 |
| EP | 1445758 | 8/2004 |
| KR | 20160063695 | 6/2016 |
| KR | 20170098788 | 8/2017 |
| WO | 2005018600 | 3/2005 |
| WO | 2005063334 | 7/2005 |
| WO | 2005075020 | 8/2005 |
| WO | 2006023498 | 2/2006 |

OTHER PUBLICATIONS

Wang et al. 2019 Int. J. Mol. Sci. 20: article 4777 15 pages (Year: 2019).*

Perez et al; "Acoustic field characterization of the Duolith: Measurements and modeling of a clinical shock wave therapy device"; J.Acoust.Soc.Am., vol. 134, No. 2, Pt. 2, Aug. 2013, pp. 1663-1674.

Carol Samuel, "An Investigation into the efficacy of reflexology on acute pain in healthy human subjects", University of Portsmouth, Jan. 2011.

Huemer, Georg M. et al; "Comparison of the effectiveness of gene therapy with transforming growth factor-B or extracorpal shock wave therapy to reduce ischemic necrosis in an epigastric skin flap model in rats"; From the Clinical Department of Plastic and Reconstructive Surgery, Cardiac Surgery, Orthopedics, and the Ludwig-Boltzmann Institute for Quality Control in Plastic Surgery, Medical University Innsbruck Austria; Feb. 13, 2004; copyright 2005 by the Wound Healing Society. ISSN: 1067-1927 (Wound Rep Reg 2005;13:262-268).

R.Meirer, et al; Extracorporal shock wave may enhance skin flap survival in an animal model; British Journal of Plastic Surgery; vol. 58, Issue 1, Jan. 2005, pp. 53-57; Copyright 2004; The British Association of Plastic Surgeons, published by Elsevier ltd.

T. Nishida, et al; Extracorporeal Cardiac Shock Wave Therapy MarKedly Ameliorates Ischemia-Induced Myocardial Dysfunction in Pigs in Vivo; Circulation; Nov. 9, 2004;Circulation. 2004; 110; pp. 3055-3061.

L.Gerdesmeyer, et al; Antibacterial Effects of Extracorporeal Shock Waves; World Fed for Ultrasound in Medicine & Biology;printed USA;Elsevier, vol. 31,No. 1, pp. 115-119, 2005.

G.Haupt, et al; Effect of Shock Waves on the Healing of Partial-Thickness Wounds in Piglets; Journal of Surgical Research, vol. 49, No. 1, pp. 45-48, Jul. 1990; Copyright 1990 by Academic Press, Inc.

Jagadeesh, G. et al;"Novel applications of micro-shock waves in biological sciences"; J. Indian Inst. Sci. 2002, 82, pp. 1-10.

Thiel, M. et al; "The use of shock waves in medicine—a tool of the modem OR; an overview of basic physical principle ?. history and research", Min Invas Ther & Allied Technol 2000; 9(3/4) 247-:253.

* cited by examiner

ACOUSTIC SHOCK WAVE OR PRESSURE PULSE TREATMENT FOR PROPTOSIS OR EXOPHTHALMOS

FIELD OF THE INVENTION

The present invention relates to a treatment for delivering acoustic shock waves or pressure pulses to eye tissue non-invasively and methods used in conjunction with the device to treat the eye tissue for swelling and inflammation. In the case of thyroid disease, the thyroid gland can also be treated directly to treat the proptosis condition.

BACKGROUND OF THE INVENTION

Proptosis, or exophthalmos, exophthalmus, exophthalmia, or exorbitism is a bulging of one or both of the eyes from their natural position. Proptosis can be a result of various health conditions; however, the most common cause of proptosis is a thyroid condition, Graves' disease, less commonly with Hashimoto's thyroiditis.

In Graves' disease, swelling, fibrosis, and scarring of the tissue behind the eye muscles surrounding the eye may occur. This crowds the bony orbit where the eye sits, causing the eyes to bulge forward. Graves' ophthalmopathy, also known as thyroid eye disease or TED, is an autoimmune inflammatory disorder of the orbit and periorbital tissues, characterized by upper eyelid retraction, lid lag, swelling, redness or erythema, conjunctivitis, and bulging eyes or exophthalmos.

The condition is part of a systemic process with variable expression in the eyes, thyroid, and skin, caused by autoantibodies that bind to tissues in those organs. The autoantibodies target the fibroblasts in the eye muscles, and those fibroblasts can differentiate into fat cells or adipocytes. Fat cells and muscles expand and become inflamed and veins become compressed and are unable to drain fluid which causes inflammation, swelling or edema.

In the present invention, a non-invasive low energy shock wave treatment is disclosed overcoming these issues.

SUMMARY OF THE INVENTION

The device of the present invention allows for a method of treating inflamed tissue behind the eye or the thyroid directly to reduce pressure and inflammation of the eye tissue using pressure pulses or shock waves.

In a first embodiment, the treatment method for bulging eyes has the steps of placing an applicator head of an acoustic shock wave or pressure pulse generator or source on or near an eye or eyelid region; coupling the applicator head directly or indirectly to an exposed surface of the region being treated; and activating the generator or source to emit pressure pulses or acoustic shock waves through the eyelid skin or eye tissue exhibiting high pressure and inflammation to reduce the pressure and inflammation.

In a second embodiment method, the inflamed and bulging eye tissue behind the eye is treated by placing the applicator head against a temple region and emitting the shock waves directed toward the inflamed and swollen eye tissue behind the eye.

In a third embodiment, the bulging eye is treated by placing the applicator on the thyroid gland to stimulate the gland to reduce the inflammation and swelling behind the eye.

In a fourth embodiment, the bulging eye is treated by employing reflexology zones for the thyroid or eye through a patient's foot or hand.

Preferably, the emitted pressure pulses or acoustic shock waves are transmitted in a pattern passing through the skin to the eye tissue. The method allows the emitted pressure pulses or acoustic shock waves pattern to impinge the eye tissue. The method has the pressure pulse being an acoustic pulse which includes several cycles of positive and negative pressure. The pressure pulse has an amplitude of the positive part of such a cycle should be above 0.1 MPa and the time duration of the pressure pulse is from below a microsecond to about a second. The rise times of the positive part of the first pressure cycle in the range of nanoseconds (ns) up to some milliseconds (ms). The pressure pulse can be the acoustic shock waves of very fast pressure pulses having amplitudes above 0.1 MPa and rise times of the amplitude being below 1000 ns. Typically, the duration of the shock wave is typically below 1-3 microseconds ($\mu s$) for the positive part of a cycle and typically above some microseconds for the negative part of a cycle.

One treatment method features subjecting the eye tissue to convergent, divergent, planar or near planar acoustic shock waves or pressure pulses in the absence of a focal point impinging the cells stimulating a cellular response in the absence of creating cavitation bubbles evidenced by not experiencing the sensation of hemorrhaging caused by the emitted waves or pulses in cells wherein the cells are positioned within an unobstructed path of the emitted shock waves or pressure pulses; and away from any localized geometric focal volume or point of the emitted shock waves wherein the emitted shock waves or pressure pulses either have no geometric focal volume or point or have a focal volume or point ahead of the cells or beyond the cells thereby passing the emitted waves or pulses through the cells while avoiding having any localized focal point within the cells of the eye tissue.

Ideally, the emitted pressure pulses or shock waves are convergent, divergent, planar or near planar and the pressure pulse shock wave generator or source is based on electrohydraulic, electromagnetic, piezoceramic or ballistic wave generation having an energy density value ranging as low as 0.00001 $mJ/mm^2$ to a high end of below 1.0 $mJ/mm^2$.

The method allows for subjecting the eye tissue or the thyroid directly to the acoustic shock waves with a low energy density of less than 1.0 $mJ/mm^2$ per shock wave to stimulate said cells or tissue wherein the cells or tissue is positioned directly within a path of the emitted pressure pulses or acoustic shock waves in the absence of any focal point or if a focal point exists, the cells or tissue being treated is positioned away from any focal point.

The method allows the energy density to be selected to avoid any cell damage to the cells or tissue. The method beneficially treats the tissue to stimulate by accelerating or increasing cell growth or regeneration wherein the administering is applied to a patient who has a pathological condition of the eyes exhibiting damage caused by injury or disease such as thyroid disease, inflammation, injury, any one of which has caused an increased pressure and inflammation which is reduced by the treatment. The method of treating the tissue stimulates the tissue by accelerating and increasing cell tissue growth or regeneration or repair in addition to reducing tissue swelling and pressure and inflammation and wherein the cell or tissue is from a mammal which is a human or an animal exhibiting an inflamed, swelling or bulging eye.

Definitions

"Adrenergic receptor", the adrenergic receptors or adrenoceptors are a class of G protein-coupled receptors that are targets of many catecholamines like norepinephrine (noradrenaline) and epinephrine (adrenaline) produced by the body, but also many medications like beta blockers, β2 agonists and α2 agonists, which are used to treat high blood pressure and asthma for example. Many cells have these receptors, and the binding of a catecholamine to the receptor will generally stimulate the sympathetic nervous system (SNS). SNS is responsible for the fight-or-flight response, which is triggered for example by exercise or fear causing situations. This response dilates pupils, increases heart rate, mobilizes energy, and diverts blood flow from non-essential organs to skeletal muscle. These effects together tend to increase physical performance momentarily.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"Exophthalmos" describes a condition where the eyeball protrudes from the eye socket, making it appear to bulge. It can affect one or both eyes. Exophthalmos is not a condition, but the sign of a disorder. Commonly, it can signal a problem with the thyroid gland. Graves' disease is the most common cause of exophthalmos.

"Extracorporeal" means occurring or based outside the living body.

A "generalized paraboloid" according to the present invention is also a three-dimensional bowl. In two dimensions (in Cartesian coordinates, x and y) the formula $y^n=2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nanoseconds (ns) up to some milliseconds (ms). Very fast pressure pulses are called shock waves. Shock waves used in medical applications do have amplitudes above 0.1 MPa and rise times of the amplitude can be below 1000 ns, preferably at or below 100 ns. The duration of a shock wave is typically below 1-3 microseconds (μs) for the positive part of a cycle and typically above some microseconds for the negative part of a cycle.

"Proptosis", also known as exophthalmos, is a bulging of one or both of the eyes.

"Shock Wave": As used herein is defined by Camilo Perez, Hong Chen, and Thomas J. Matula; Center for Industrial and Medical Ultrasound, Applied Physics Laboratory, University of Washington, 1013 NE 40th Street, Seattle, Washington 98105; Maria Karzova and Vera A. Khokhlovab; Department of Acoustics, Faculty of Physics, Moscow State University, Moscow 119991, Russia; (Received 9 Oct. 2012; revised 16 Apr. 2013; accepted 1 May 2013) in their publication, "Acoustic field characterization of the Duolith: Measurements and modeling of a clinical shock wave therapy device"; incorporated by reference herein in its entirety.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1:
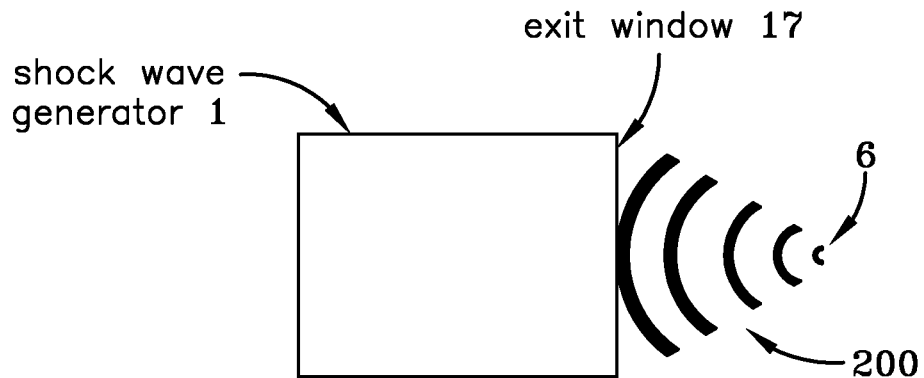
FIG. 1 is a simplified depiction of a pressure pulse/shock wave (PP/SW) generator with focusing wave characteristics.
Figure 2:
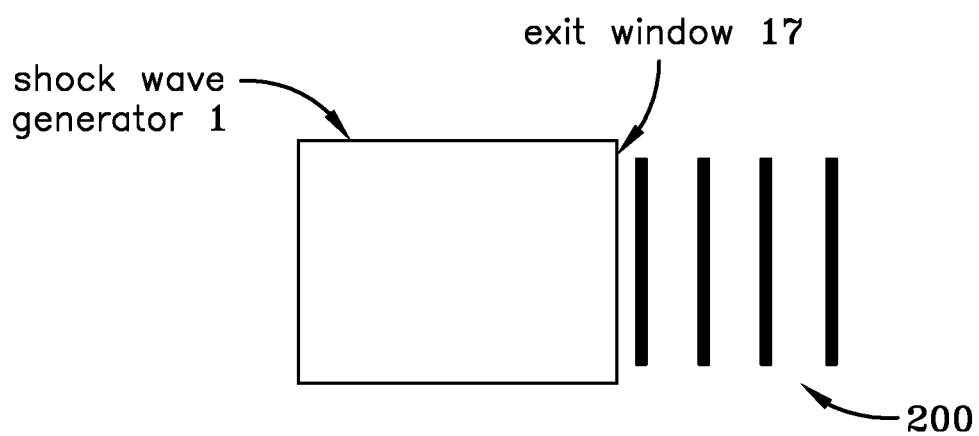
FIG. 2 is a simplified depiction of a pressure pulse/shock wave generator with plane wave characteristics.
Figure 3:
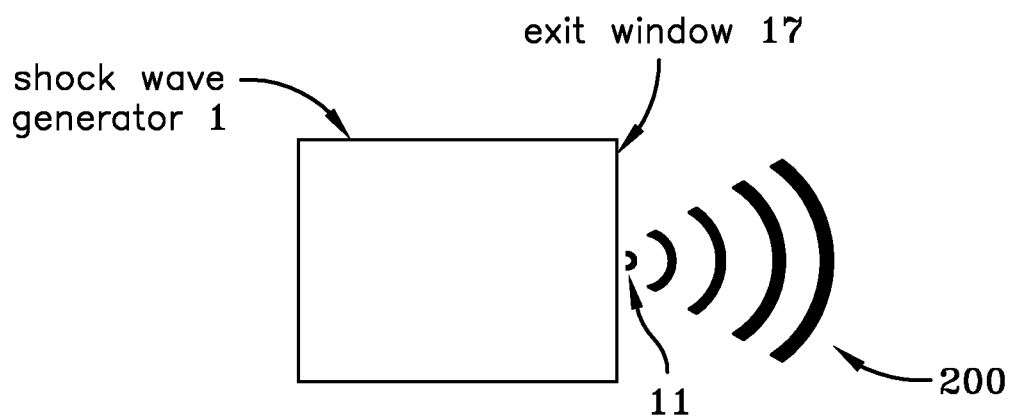
FIG. 3 is a simplified depiction of a pressure pulse/shock wave generator with divergent wave characteristics.

With reference to FIGS. 1-3, a variety of schematic views of acoustic shock waves or pressure pulses are described. The following description of the proper amplitude and pressure pulse intensities of the shock waves are provided along with a description of how the shock waves actually function. For the purpose of describing, the shock waves were used as exemplary and are intended to include all of the wave patterns discussed in the figures as possible treatment patterns.

FIG. 1 is a simplified depiction of a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The affected tissue or organ is generally located in or near the focal point which is located in or near position 6. At position 17 a water cushion or any other kind of exit window for the acoustical energy is located.

FIG. 2 is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even, also referred to herein as "disturbed", wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

FIG. 3 is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 3, the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup.

Figure 4:
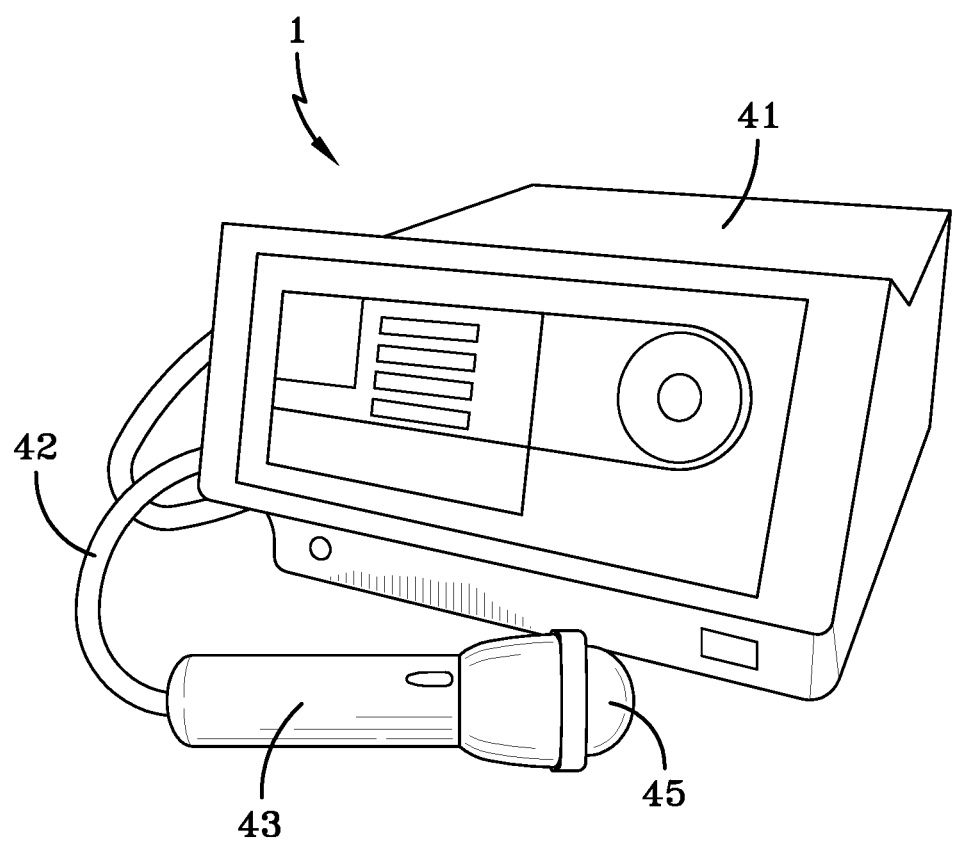
FIG. 4 is a simplified depiction of a pressure pulse/shock wave generator connected to a control/power supply unit.

With reference to FIG. 4, an exemplary acoustic shock wave apparatus 1 is illustrated. The shock wave apparatus 1 has a generator 41 connected by a flexible hose with fluid conduits extending from the shock wave generator 41 to an applicator 43 which transmits the acoustic waves when coupled to the skin by using a fluid or acoustic gel. The applicator 43 as illustrated has a body that enables a technician to hold the applicator 43 and as illustrated this applicator is an electrohydraulic that is filled with fluid to facilitate the transmission of the shock waves. The fluid expands a flexible membrane in such a fashion that the membrane extends outwardly in a balloon shape fashion as illustrated in FIG. 4. As shown, this type of applicator 43 has a hydraulic spark generator using either focused or unfocused shock waves, preferably in a low energy level, less than the range of 0.01 mJ/mm$^2$ to 0.3 mJ/mm$^2$. The flexible hose 42 is connected to a fluid supply that fills the applicator 43 and expands the flexible membrane when filled. Alternatively, a ballistic, piezoelectric or spherical acoustic shock wave device can be used to generate the desired waves.

Figure 5:
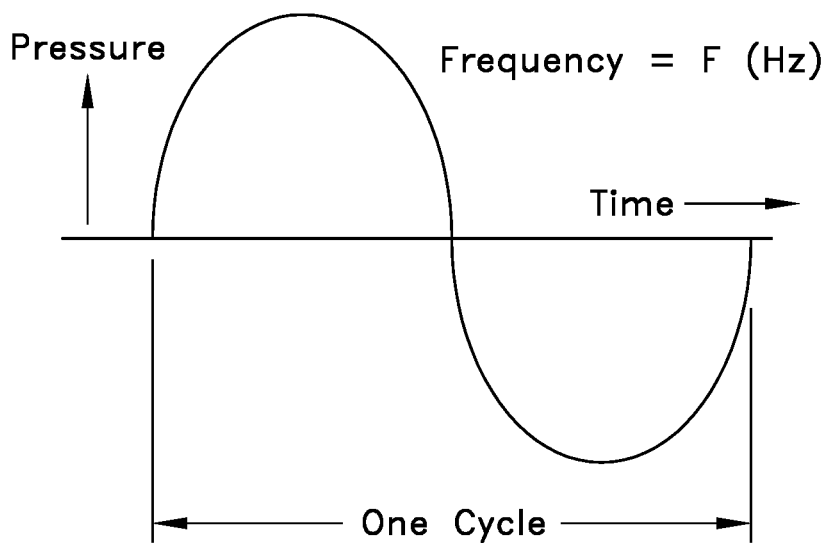
FIG. 5 is a graph showing an exemplary ultrasound wave pattern.
Figure 6:
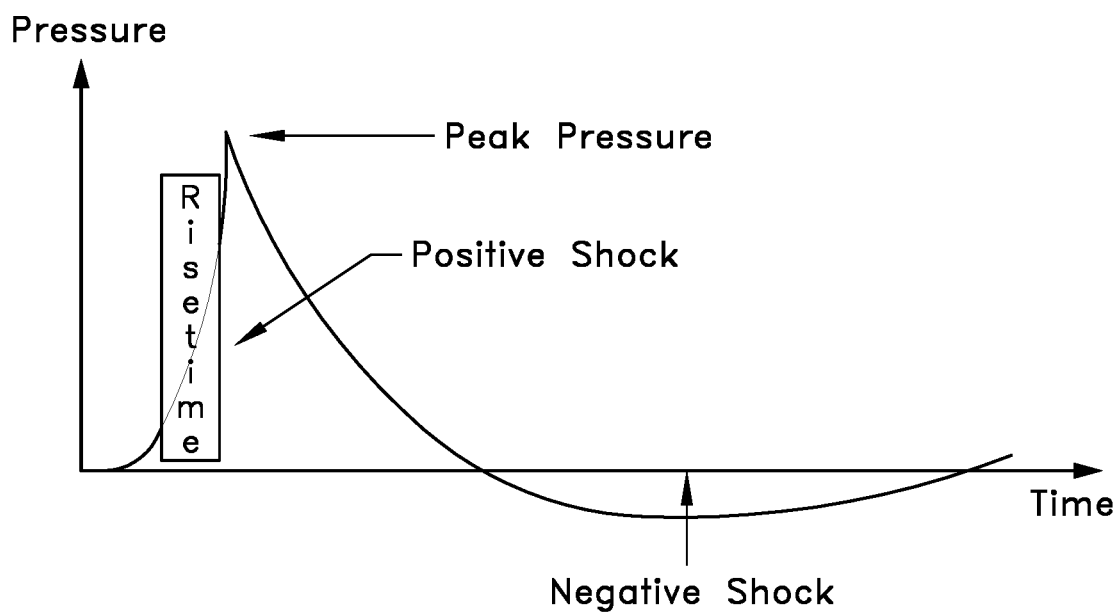
FIG. 6 is a graph of an exemplary acoustic shock wave pattern.

The ultrasonic wave pattern shown in FIG. 5 is contrasted to an asymmetric acoustic wave pattern which is illustrated in FIG. 6. As shown, ultrasound waves are symmetrical having the positive rise time equal to the negative in a sinusoidal wave form. These ultrasound waves generate heat in the tissue and are accordingly believed not suitable for use on organs or eye tissue.

Figure 7:
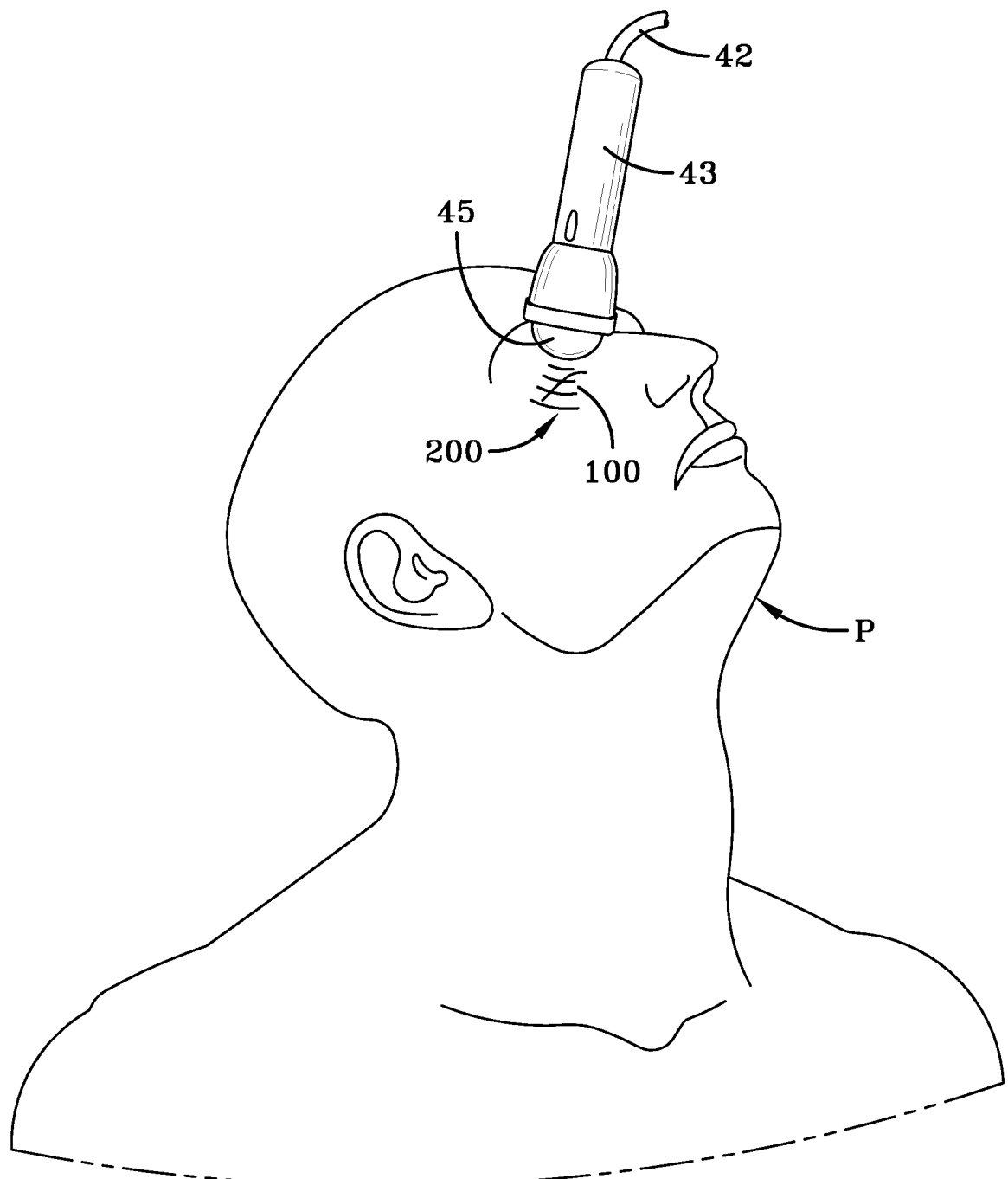
FIG. 7 shows a patient being treated extracorporeally with shock waves being transmitted through the skin and eye tissue to the region to be treated.

FIG. 7 is a depiction of an acoustic shock wave treatment to a region of the eyelid or eye 100 to reduce swelling or inflammation. The acoustic shock waves 200 are transmitted through the eyelid skin as shown.

Figure 8:
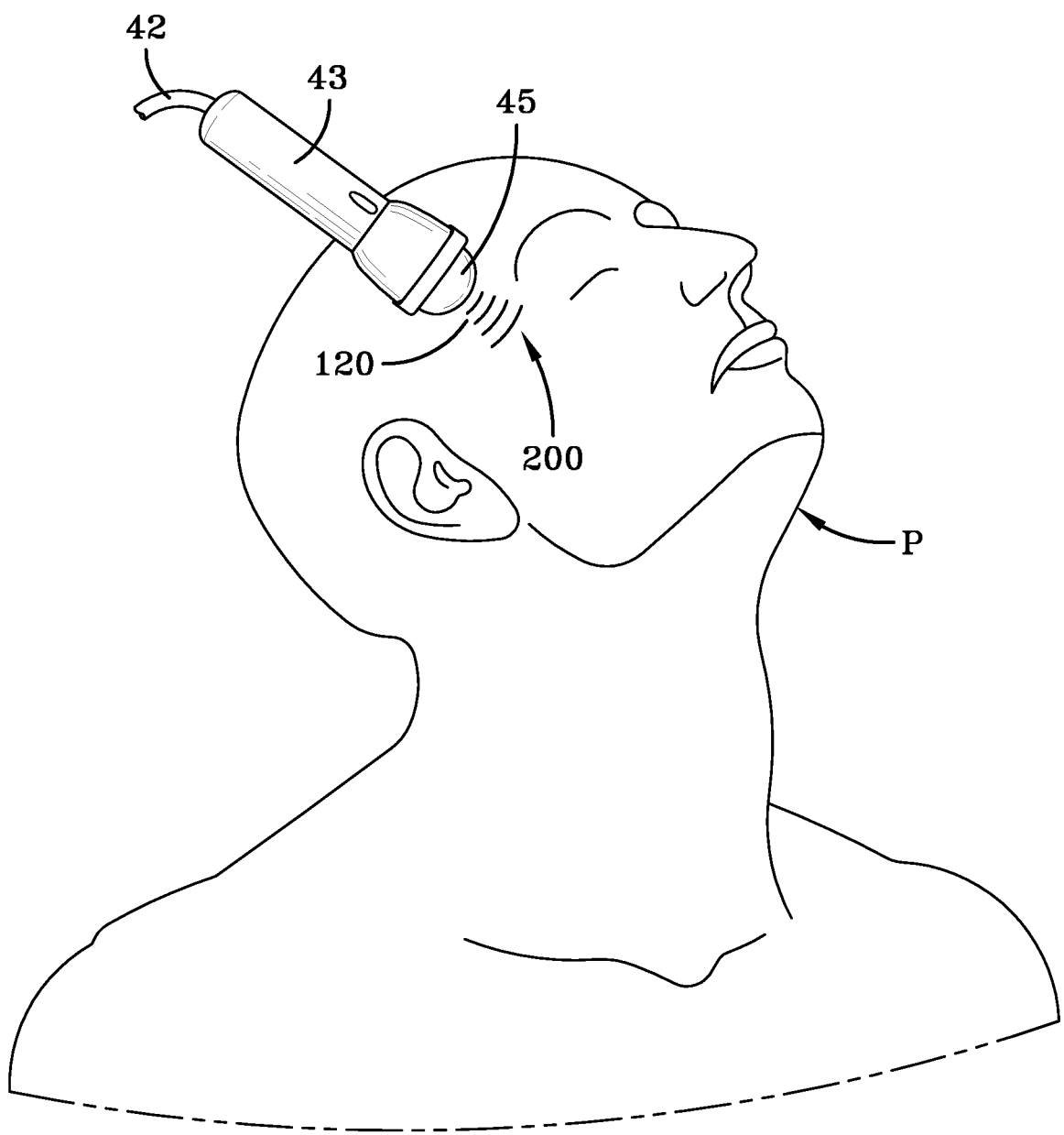
FIG. 8, shows a patient being treated extracorporeally with shock waves being transmitted through the eyelid skin to the eye tissue with the applicator positioned at the temple of the patient being treated.

As shown in FIG. 8, the eye tissue can be targeted with the applicator positioned at the temple 120 of the patient P being treated.

Figure 9:
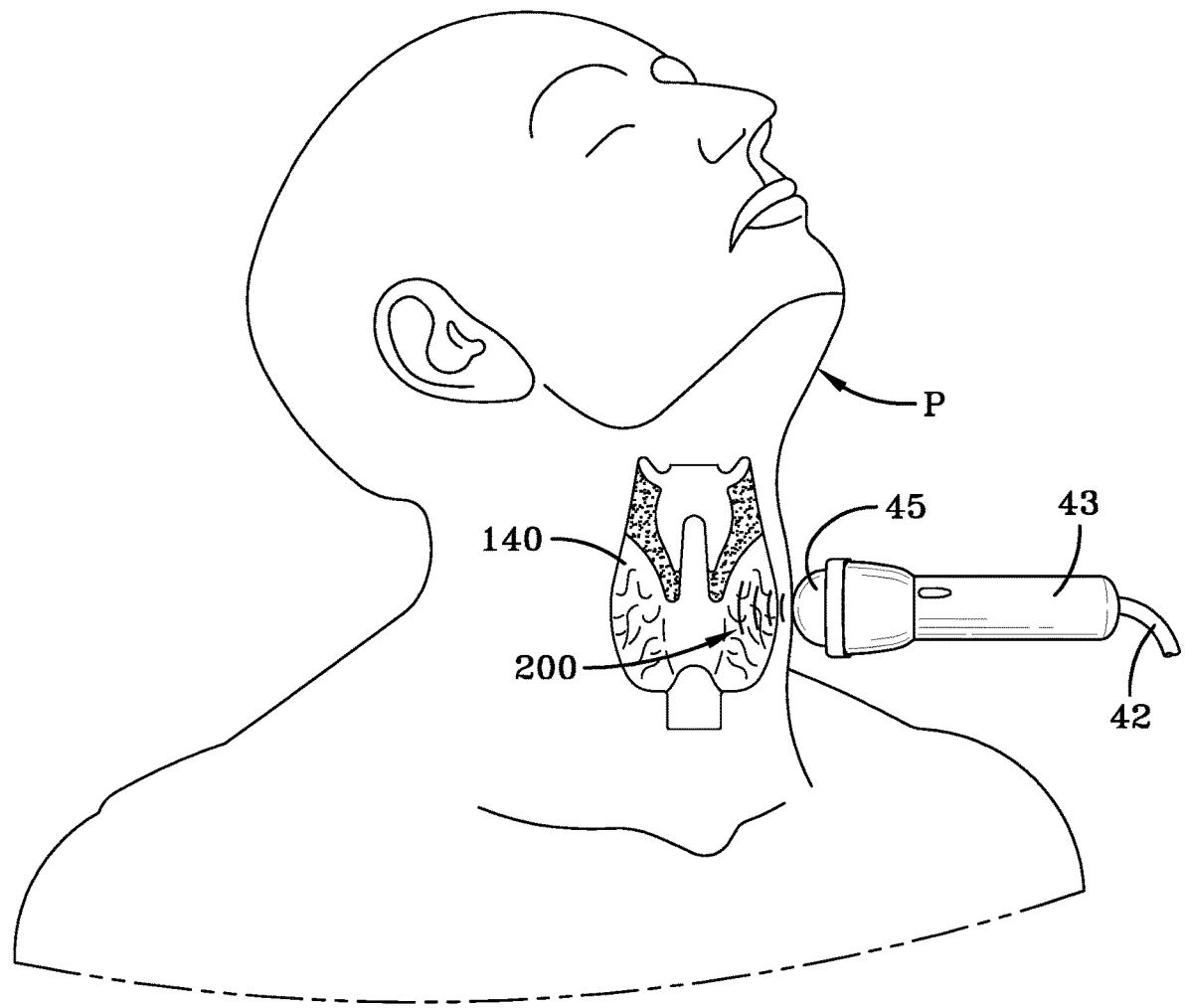
FIG. 9 shows a patient being treated extracorporeally with shock waves being transmitted through the skin to the tissue of the thyroid directly to cause a regulation of the thyroid to reduce the proptosis condition.

As shown in FIG. 9, the tissue of the thyroid 140 can also be targeted directly to cause a regulation of the thyroid 140 to reduce the proptosis condition.

Figure 10:
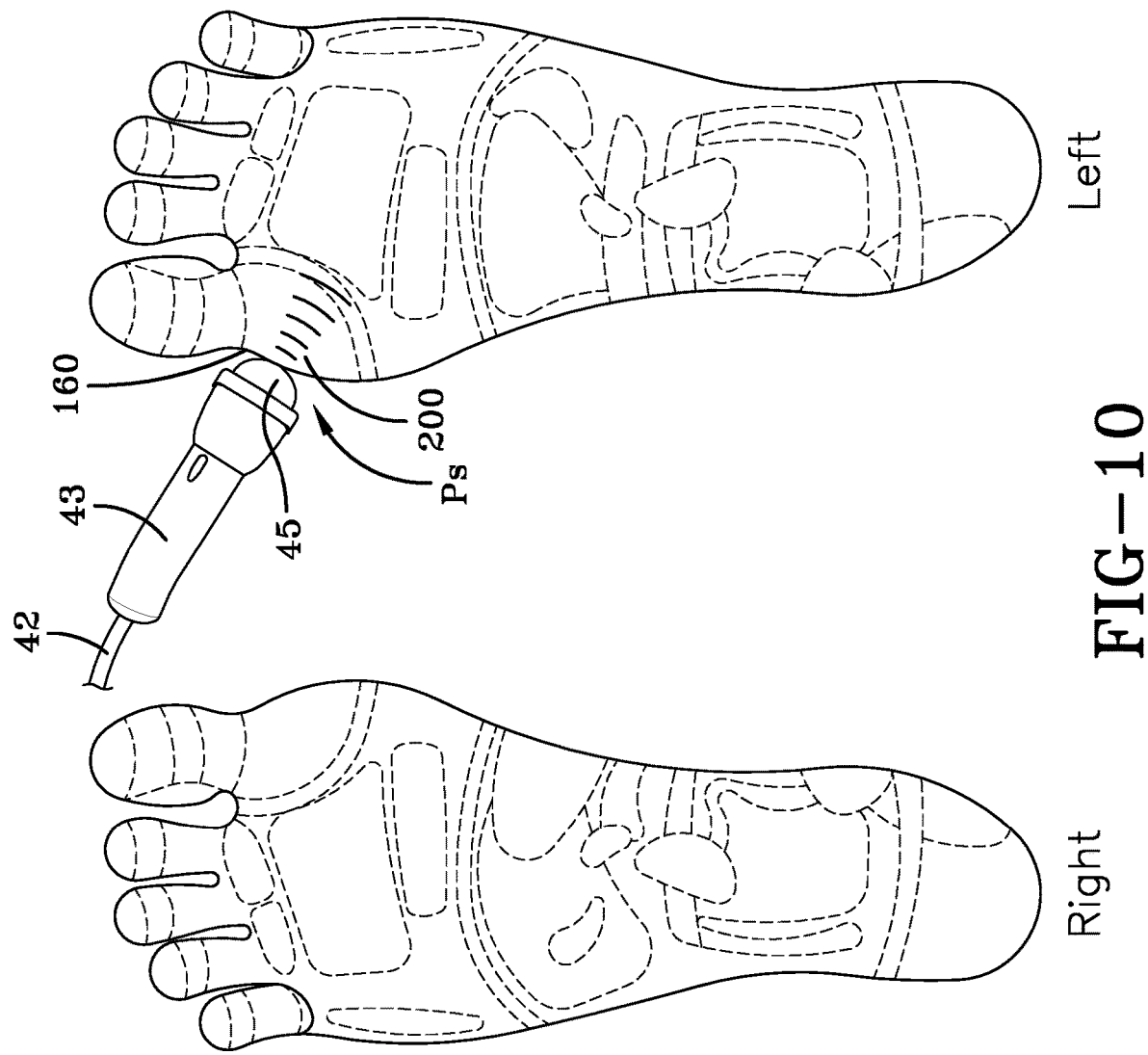
FIG. 10 shows the shock wave generator device directed at a reflexology zone on a foot of a patient.

FIG. 10 is a perspective view of a foot of a patient whose reflexology zone or target 160 for the eye or thyroid is being treated. A shock wave applicator head 43 is brought into contact with the skin Ps preferably an acoustic gel is used to enhance the transmission of the shock waves 200 through the skin Ps. The shock wave applicator head 43 can be handheld and manipulated across the skin Ps to drive the shock waves 200 in the direction the shock wave head 43 is pointed to activate a stimulating response through the reflexology zone 160.

As illustrated, the device shown is an electrohydraulic acoustic shock wave generator, however, other devices that generate acoustic shock waves can be used. Ultrasonic devices may be considered, but there is no data to support a sinusoidal wave form would work and therefore not considered as effective as the asymmetric wave generators. The acoustic shock waves activate a cellular response within the reflexology treatment site. This response or stimulation causes an increase of nitric oxide and a release of a variety of growth factors such as VEGF. As shown, the flexible membrane is protruding outward and the applicator 43 has been filled with fluid, the transmission or emission of acoustic shock waves 200 is directed towards the reflexology zone 160. In order to accomplish a good transmission, it is important the flexible membrane be pressed against the patient's P skin Ps and as indicated coupling gels may be used. The zone 160, as illustrated, is the reflexology zone for the pancreas which is a region of the foot located in a middle of an inside arch of each foot. By transmitting the shock waves 200 to the zone 160, is it believed that a modulation of the secretions from the pancreas can be made. This modulation or adjustment is achieved by transmitting the acoustic waves 200 at low energy directly onto the zone 160.

Figure 11:
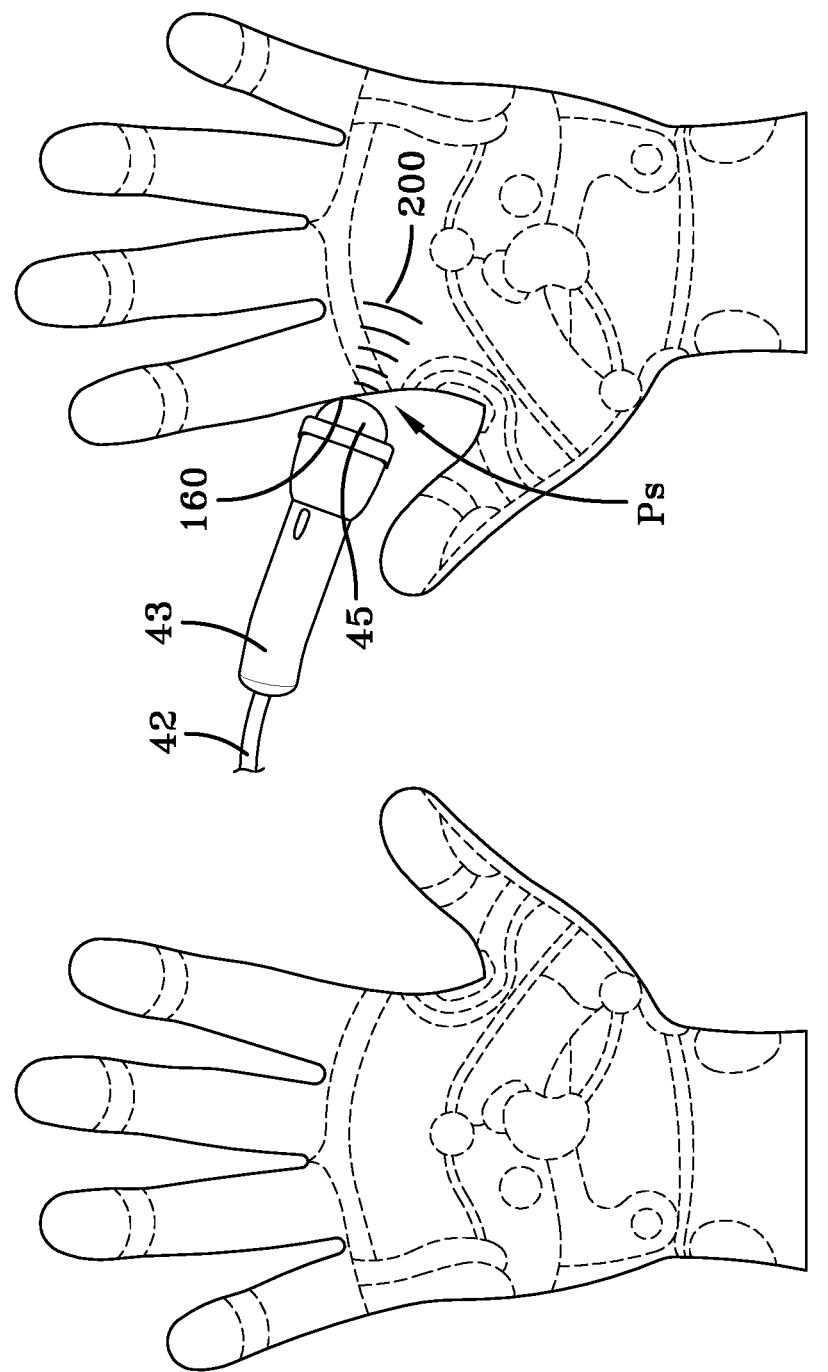
FIG. 11 shows the shock wave generator device directed at a reflexology zone on a hand of a patient.

With reference to FIG. 11, a view of a hand of a patient whose reflexology zone 160 is being treated with acoustic shock waves 200 is illustrated. In this illustration, it is important to note that the applicator 43 presses against the skin Ps of the hand in the reflexology zone 160 for the thyroid which is a region of the hand between the index finger and thumb.

Figure 12:
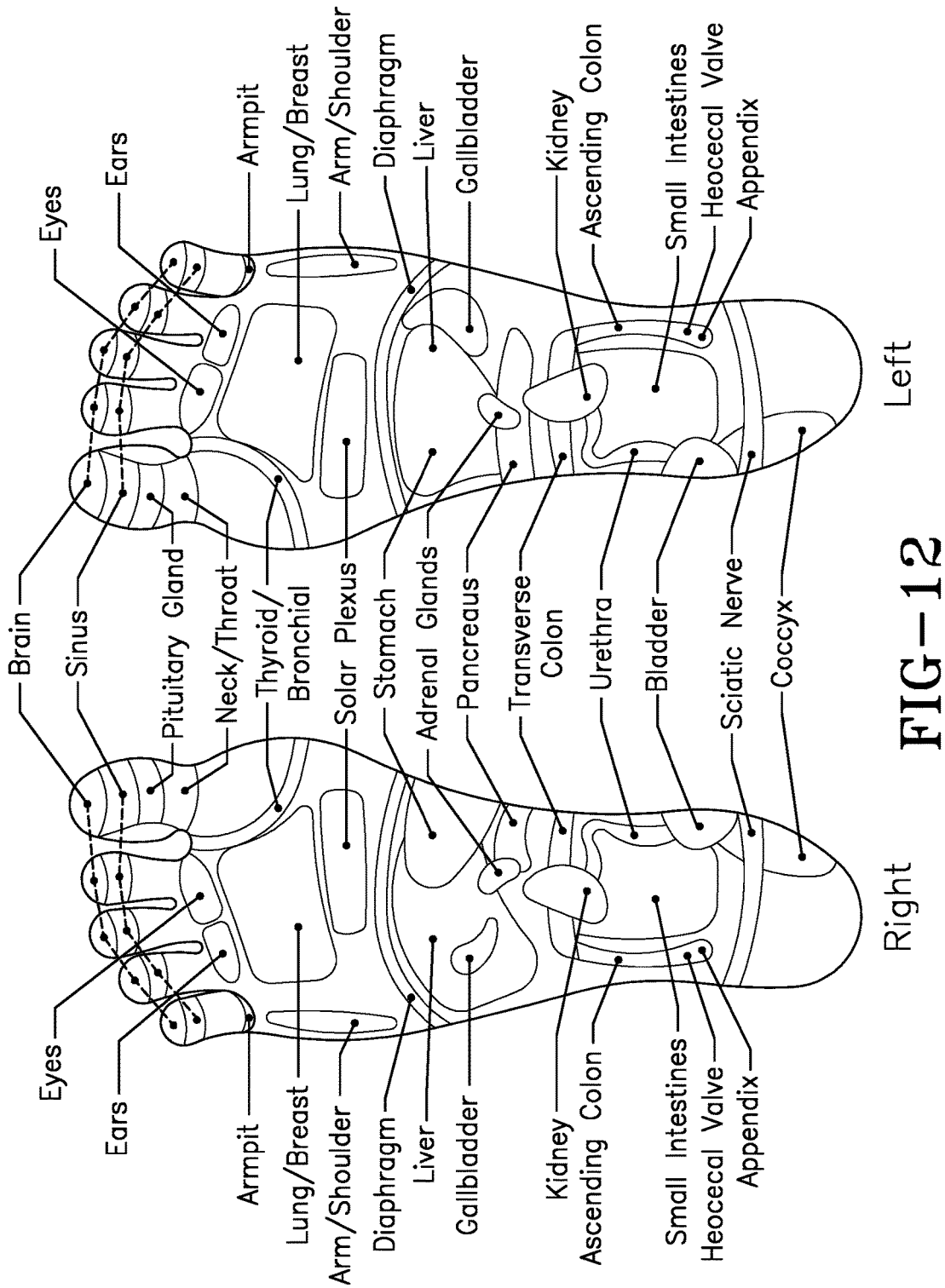
FIG. 12 shows a schematic view showing general reflexology locations of the foot in the human body.

With reference to FIG. 12, a reflexology foot chart is shown detailing the various zones that correspond to organs, glands etc. of the body.

Figure 13:
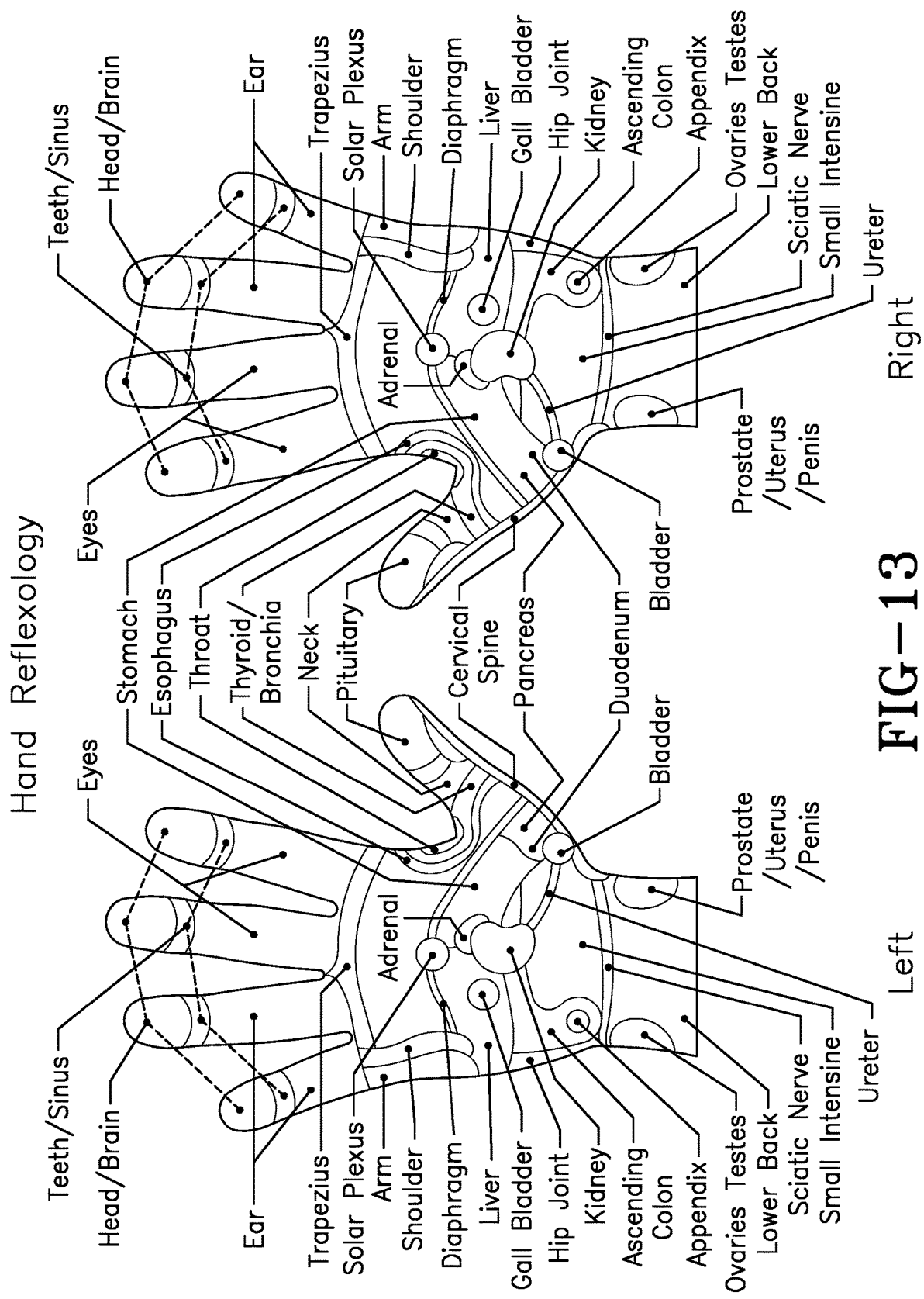
FIG. 13 shows a schematic view showing general reflexology locations of the hand in the human body.

With reference to FIG. 13, a reflexology hand chart is shown detailing the various zones that correspond to organs, glands etc. of the body.

It is believed that modulation and beneficial adjustment can be achieved at reflexology zones for stimulating, modulating or adjusting reflexology zones for glands or organs such as the liver, kidney or any of those indicated in FIG. 12 for the foot zones and FIG. 13 for the hand zones will create a systemic anti-aging response. It is further believed that the hybrid Eastern medical acupuncture treatments or massages historically used are far less effective and less reliable than the results achieved by the deeper tissue penetrating transmission that are achieved by acoustic shock wave therapy applied to these reflexology zones.

This apparatus, in certain embodiments, may be adjusted/modified/or the complete shock wave head or part of it may be exchanged so that the desired and/or optimal acoustic profile such as one having wave fronts with focused, planar, nearly plane, convergent or divergent characteristics can be chosen.

This apparatus may, in certain embodiments, be adjusted/modified/or the complete shock wave head or part of it may be exchanged so that the desired and/or optimal acoustic profile such as one having wave fronts with focused, planar, nearly plane, convergent or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion which houses water which defines the path of pressure pulse waves that is, through which those waves are transmitted. In a preferred embodiment, a patient is coupled via ultrasound gel or oil to the acoustic exit window 17, which can, for example, be an acoustic transparent membrane, a water cushion, a plastic plate or a metal plate.

These shock wave energy transmissions are effective in stimulating a cellular response and can be accomplished without creating the cavitation bubbles in the tissue of the target site when employed in other than site targeted high energy focused transmissions. This effectively insures the tissue does not have to experience the sensation of hemorrhaging so common in the higher energy focused wave forms having a focal point at or within the targeted treatment site. Bleeding internally causes an increase in fluid pressure which can lead to increased damage. This can be completely avoided in this treatment protocol.

The fact that some if not all of the dosage can be at a low energy the common problem of localized hemorrhaging is reduced making it more practical to administer multiple dosages of waves from various orientations inside the mouth to further optimize the treatment and cellular stimulation of the target site. Heretofore focused high energy multiple treatments induced pain and discomfort to the patient. The use of low energy focused or un-focused waves at the target site enables multiple sequential treatments.

The present method may need precise site location and can be used in combination with such known devices as ultrasound, cat-scan or x-ray imaging if needed. The physician's general understanding of the anatomy of the patient may be sufficient to locate the target area to be treated. This is particularly true when the device is visually within the surgeon's line of sight and this permits the lens or cover of the emitting shock wave source to impinge on the affected tissue directly through a transmission enhancing gel, water or fluid medium during the pressure pulse or shock wave treatment. The treated area can withstand a far greater number of shock waves based on the selected energy level being emitted. For example, at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of surrounding cell hemorrhaging and other kinds of damage to the surrounding cells or tissue while still providing a stimulating stem cell activation or a cellular release or activation of proteins such as VEGF and other growth factors while simultaneously germicidally attacking the degenerative tissue or infectious bacteria at the target site.

Due to the wide range of beneficial treatments available it is believed preferable that the optimal use of one or more wave generators or sources should be selected on the basis of the specific application. A key advantage of the present inventive methodology is that it is complimentary to conventional medical procedures. In the case of any operative surgical procedure the surgical area of the patient can be bombarded with these energy waves to stimulate cellular release of healing agents and growth factors. This will dramatically reduce the healing process time. Most preferably such patients may be provided more than one such treatment with an intervening dwell time for cellular relaxation prior to secondary and tertiary post operative treatments.

The underlying principle of these pressure pulse or shock wave therapy methods is to enrich the treatment area directly and to stimulate the body's own natural healing capability. This is accomplished by deploying shock waves to stimulate strong cells in the surrounding tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly, not only can the energy intensity be reduced in some cases, but also the number of applied shock wave impulses can be lowered from several thousand to as few as one or more pulses and still yield a beneficial stimulating response. The key is to provide at least a sufficient amount of energy to activate healing reactions.

The use of shock waves as described above appears to involve factors such as thermal heating, light emission, electromagnetic field exposure, chemical releases in the cells as well as a microbiological response within the cells.

The unfocused shock waves can be of a divergent wave pattern, planar or near planar pattern preferably convergent diffused or far-sighted wave pattern, of a low peak pressure amplitude and density. Typically, the energy density values range as low as 0.000001 mJ/mm$^2$ and having a high end energy density of below 1.0 mJ/mm$^2$, preferably 0.20 mJ/mm$^2$ or less. The peak pressure amplitude of the positive part of the cycle should be above 1.0 and its duration is below 1-3 microseconds.

The treatment depth can vary from the surface to the full depth of the treated organ. The treatment site can be defined by a much larger treatment area than the 0.10-3.0 cm$_2$ commonly produced by focused waves. The above methodology is particularly well suited for surface as well as sub-surface soft tissue organ treatments like the eye.

While the above listed indications cited above are not exhaustive nor intended to be limiting, it is exemplary of the wide range of beneficial uses of high energy focused or low energy and amplitude unfocused divergent, planar or nearly planar shock waves, convergent shock waves, diffused shock waves or a combination of shock wave types in the treatment of humans and other mammals that are exposed to a neurological trauma or disease affecting the nervous system or are at high risk to be so exposed as the result of a high potential genetic pre-disposition to such diseases.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of treating a patient exhibiting proptosis of an eye to reduce pressure and inflammation of tissue behind the eye causing said proptosis using pressure pulses or shock waves comprises the steps of:
   placing an applicator head of an acoustic shock wave or pressure pulse generator or source at a temple of the patient adjacent to the eye;
   coupling the applicator head directly to an exposed surface of skin at the temple; and
   activating the generator or source to emit pressure pulses or acoustic shock waves to impinge upon cells of the tissue behind the eye to reduce said pressure and inflammation of the tissue.

2. The method of claim 1, wherein the emitted pressure pulses or acoustic shock waves are transmitted in a pattern passing through the skin at the temple.

3. The method of claim 1, wherein the pressure pulses are each an acoustic pulse which includes several cycles of positive and negative pressure.

4. The method of claim 3, wherein each of the pressure pulses has:
   an amplitude of the positive part of such a cycle should be above 0.1 MPa; and
   a time duration from below a microsecond to a second.

5. The method of claim 4, wherein the rise times of the positive part of the first pressure cycle in the range of nanoseconds (ns) up to milliseconds (ms).

6. The method of claim 5 wherein the acoustic shock waves have amplitudes above 0.1 MPa and rise times of the amplitude below 1000 ns.

7. The method of claim 1, wherein each of the shock waves has a duration of:
   below 1-3 microseconds (µs) for the positive part of a cycle thereof; and
   longer for the negative part of the cycle.

8. The method of claim 1, wherein:
   said activating includes subjecting the tissue to convergent, divergent, planar or near planar acoustic shock waves or pressure pulses in the absence of a focal point impinging the cells of the tissue for stimulating a cellular response in the absence of creating cavitation bubbles;
   the cells are positioned within a path of the emitted shock waves or pressure pulses and away from any localized geometric focal volume or point of the emitted shock waves;

the emitted shock waves or pressure pulses either have no geometric focal volume or point or have a focal volume or point ahead of the cells or beyond the cells thereby passing the emitted waves or pulses through the cells while avoiding having any localized focal point within the cells.

9. The method of claim 1, wherein:

the emitted pressure pulses or shock waves are convergent, divergent, planar or near planar; and the pressure pulse shock wave generator or source is based on electro-hydraulic, electromagnetic, piezoceramic or ballistic wave generation having an energy density value ranging as low as 0.00001 mJ/mm$^2$ to a high end of below 1.0 mJ/mm$^2$.

10. The method of claim 9, wherein:

said activating include subjecting the eye tissue directly to the acoustic shock waves;

the acoustic shock waves have a low energy density of less than 1.0 mJ/mm$^2$ per shock wave; and the cells or tissue is positioned one of directly within a path of the emitted pressure pulses or acoustic shock waves in the absence of any focal point of the emitted pressure pulses or acoustic shock waves and the cells or tissue being treated is positioned away from the focal point if the focal point exists.

11. The method of claim 10, wherein the energy density is selected to avoid any cell damage to the cells or tissue.

* * * * *